United States Patent [19]

Papp

[11] Patent Number: 5,120,419

[45] Date of Patent: Jun. 9, 1992

[54] PHOTOELECTRIC ELECTROPHORESIS CONTROLLER

[76] Inventor: Andrew Papp, 12012 Goshen Ave., #103, West Los Angeles, Calif. 90049

[21] Appl. No.: 541,626

[22] Filed: Jun. 21, 1990

[51] Int. Cl.⁵ .......................................... G01N 27/26
[52] U.S. Cl. ............................ 204/299 R; 204/180.1; 204/182.8
[58] Field of Search ............... 204/180.1, 182.8, 299 R

[56] References Cited

U.S. PATENT DOCUMENTS

| | | | |
|---|---|---|---|
| 3,649,498 | 3/1972 | Pretorius et al. | 204/299 R |
| 3,723,712 | 3/1973 | Komline, Sr. et al. | 204/299 R |
| 4,354,116 | 10/1982 | Tsukamoto et al. | 250/576 |
| 4,707,235 | 11/1987 | Englert et al. | 204/182.8 |
| 4,909,920 | 3/1990 | Sarrine et al. | 204/299 R |

OTHER PUBLICATIONS

Al-Jorani, et al., "A mobile phase sensor for use in the development of thin-layer Chromatograms", *Laboratory Practice*, 31(3) pp. 213-214 (1982).
Stratagene Product Literature, 1990.

*Primary Examiner*—John Niebling
*Assistant Examiner*—David G. Ryser

[57] ABSTRACT

A photoelectric electrophoresis controller triggered by molecular samples and/or molecular marker dyes sensed by photodetector means when reaching determined position in a matrix, characterized by an observing photocell spaced from a reference photocell for comparison, and sampling by electronic means rejecting spurious signals, with control to respond with a detection signal to user-specified light transmission increased or decreased by the sample and/or molecular marker.

18 Claims, 2 Drawing Sheets

PHOTOELECTRIC ELECTROPHORESIS CONTROLLER

BACKGROUND OF THE INVENTION

Electrophoretic procedures provide for the analytic or preparative separation of mixtures based on molecular size, charge, and/or affinity for the electrophoresis matrix. Analytic and preparative procedures require that the separation of the position of molecules proceeds to a given degree, long enough in time that components of the mixture are resolved from each other, and short enough that desired components are not lost by running off the end of the separation matrix. Traditionally, visible of fluorescent markers, with molecular properties similar to those of difficult to visualize samples, are added to the mixture, the positions of these marker molecules are monitored by a human operator, and electrophoresis is terminated when said markers reach positions indicating that the desired separation has taken place. This provides the most accurate indication of the progress of separation, since variabilities in the voltage, current, temperature, and matrix pore size affect the mobility of the markers to the same extent that they do the samples. Thus, under variable conditions of electrophoresis, marker mobility is a better predictor than time of sample mobility. A limitation of this strategy is that a human operator must be present to periodically monitor the migration of the molecular markers and terminate electrophoresis at the appropriate time, which can range from minutes to days, depending upon application.

A typical electrophoresis apparatus consists of a slab of electrophoresis matrix and rigid support on one or more sides of the matrix. Matrix and supports are usually constructed of relatively clear materials so that molecular markers can be seen or visualized. An electric power supply is connected to the matrix via electrodes such that a direct current can be maintained across the slab. Electrodes generally consist of a conductive metal immersed in a conductive liquid. Samples mixtures are loaded into indentations, termed wells, formed at one end of the matrix. Samples are drawn toward the opposite end of the matrix by electrostatic interactions at a rate related to their physical properties. As in the case of the Automatic Isolator of Blood Plasma disclosed in U.S. Pat. No. 4,354,116 issued to Tsukamoto et al. Oct. 12, 1982, this arrangement provides access for the photodetector in this invention to take the place of human eyes in the monitoring of molecular marker or sample positions and for electronic circuitry to automate electrophoresis control (See FIG. 1).

The photoelectric elecrophoresis controller of the present invention eliminates the tedium of a human operator periodically checking on the progress of separation as well as the risk that often priceless analytical samples are lost due to carelessness. This controller provides these advantages in a much less complicated and much less expensive manner than the Computer-analyzed Vidicon Scanner system disclosed in U.S. Pat. No. 3,723,712 entitled Method for Agglomeration Measuring and Control issued to Komline et al. Mar. 27, 1973. The embodiment described herein is particularly versatile and convenient. Because the preferred embodiment optionally compares the light falling on a pair of spaced broad-spectrum Cadmium Sulfide photocells, said embodiment is able to detect the presence of virtually any sample, stained sample, or reference molecular dye marker that the eye can see and which the photocells can detect; it is thus compatible with a wide variety of electrophoresis protocols involving samples and molecular markers with different spectral properties. Because detection is based on a comparison to a reference photocell, virtually any broad-spectrum light source, present even at a varying intensity, including ambient light, will suffice for accurate detection; thus, the small photodetector occupies space on only one side of the electrophoresis apparatus, making it compatible with an apparatus of any thickness. Furthermore, detection by comparison can offer greater sensitivity than a system relying on absolute detection.

SUMMARY OF THE INVENTION

The object of this invention is to provide a novel and efficient method and apparatus for the accurate automated determination of the progress of electrophoretic separation and for the automated control of the electrophoresis upon sufficient progress. In this method, photodetector circuitry monitors the position of samples or molecular markers and ultimately controls electrophoresis by regulating or terminating the supply of electric potential or current to the electrophoresis apparatus, alerting a human operator of said progress, and/or providing a signal to other equipment for the automated further processing of electrophoresed samples.

The foregoing and various other objects and features of this invention will be apparent and fully understood from the following detailed description of the typical preferred forms and applications thereof, throughout which description reference is made to the accompanying drawings in which:

THE DRAWINGS

PREFERRED EMBODIMENT

A photoelectric electrophoresis controller is provided in which light-absorbing or light-emitting samples or molecular markers trigger an automatic operation when reaching a position determined by the placement of a photodetector arrangemnet. The photodetector arrangement consists of an observing photocell and a reference photocell nearby, such that the outputs of the photocells can be compared. A sampling circuit rejects spurious signals from the photodetector arrangement and provides accepted signals to a counter. Means are provided for electrophoresis control after a user-specified number of signals are counted, including automatic shut-off of electric current to the electrophoresis apparatus, an audible alarm capable of signaling a human operator, and a logic output capable of signaling the detection to automated devices for further preparation of the electrophoresed sample or notification of human operators in remote locations.

An invention having these purposes is described below with one example of a preferred embodiment. Although horizontal electrophoresis is shown, vertical electrophoresis can be practiced which is similar but the apparatus turned 90 degrees and supported on both sides of the slab. Another configuration in which the photoelectric electrophoresis controller can be used is capillary electrophoresis, where the slab is replaced by matrix in a capillary tube.

Figure 1:
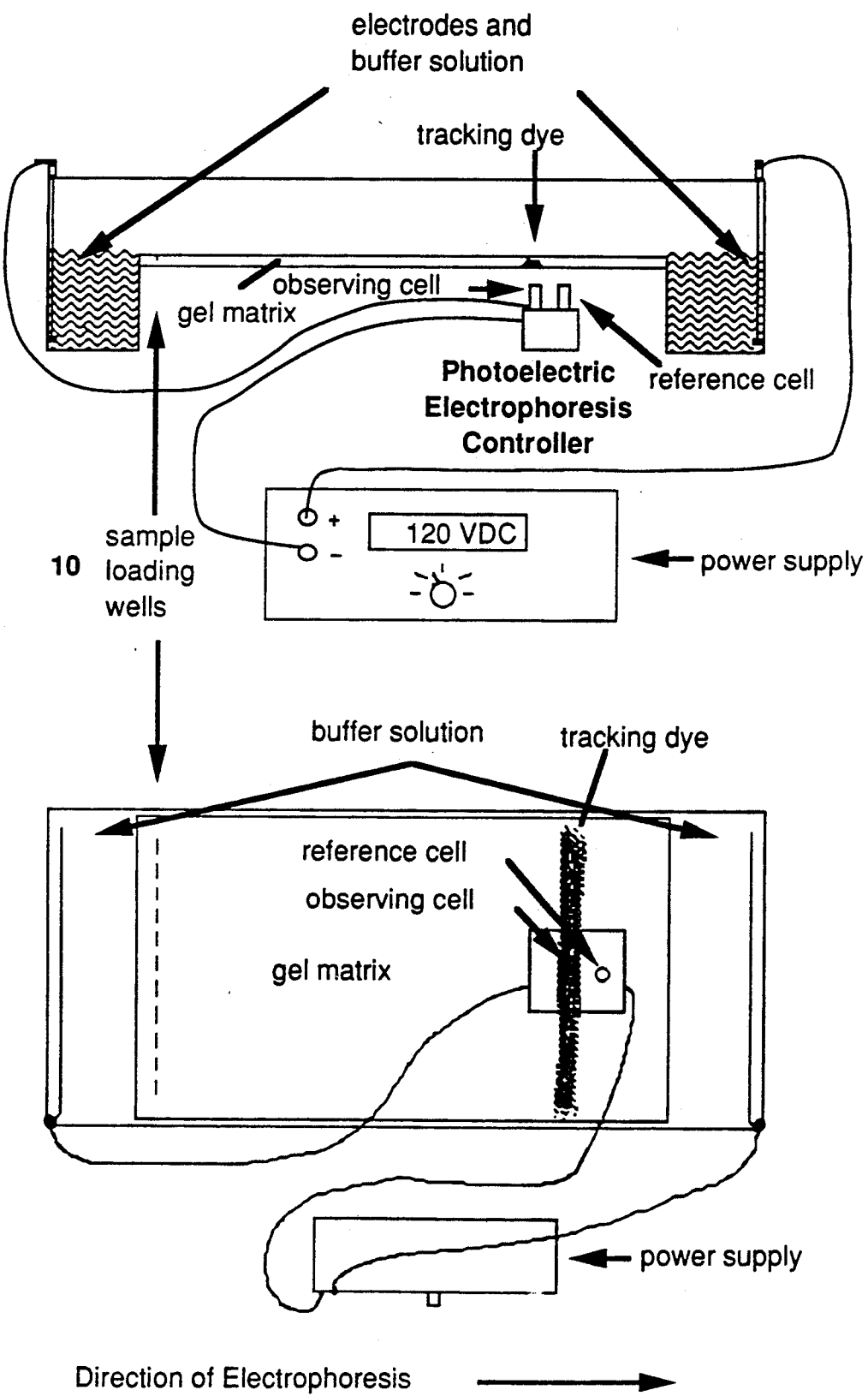
FIG. 1 shows a typical horizontal electrophoresis apparatus in an arrangement with its power supply.

A horizontal electrophoresis apparatus is shown in FIG. 1 with longitudinally spaced observing and reference photocells positioned beneath a matrix. The samples and/or molecular marker dyes electrophorese from the wells at position 10 to a position over a first photocell, the observing photocell. Accordingly, the opaqueness of sample and/or molecular marker dyes partially obstructs light from above; thus, less light falls on the observing photocell relative to a second photocell, the reference photocell. Under said circumstances, the circuit next described breaks the current flow from the power supply to the electrophoresis apparatus, sounds an audible alarm, and/or triggers another device to further process the samples in the matrix gel, and/or page remote human operators.

Figure 2:
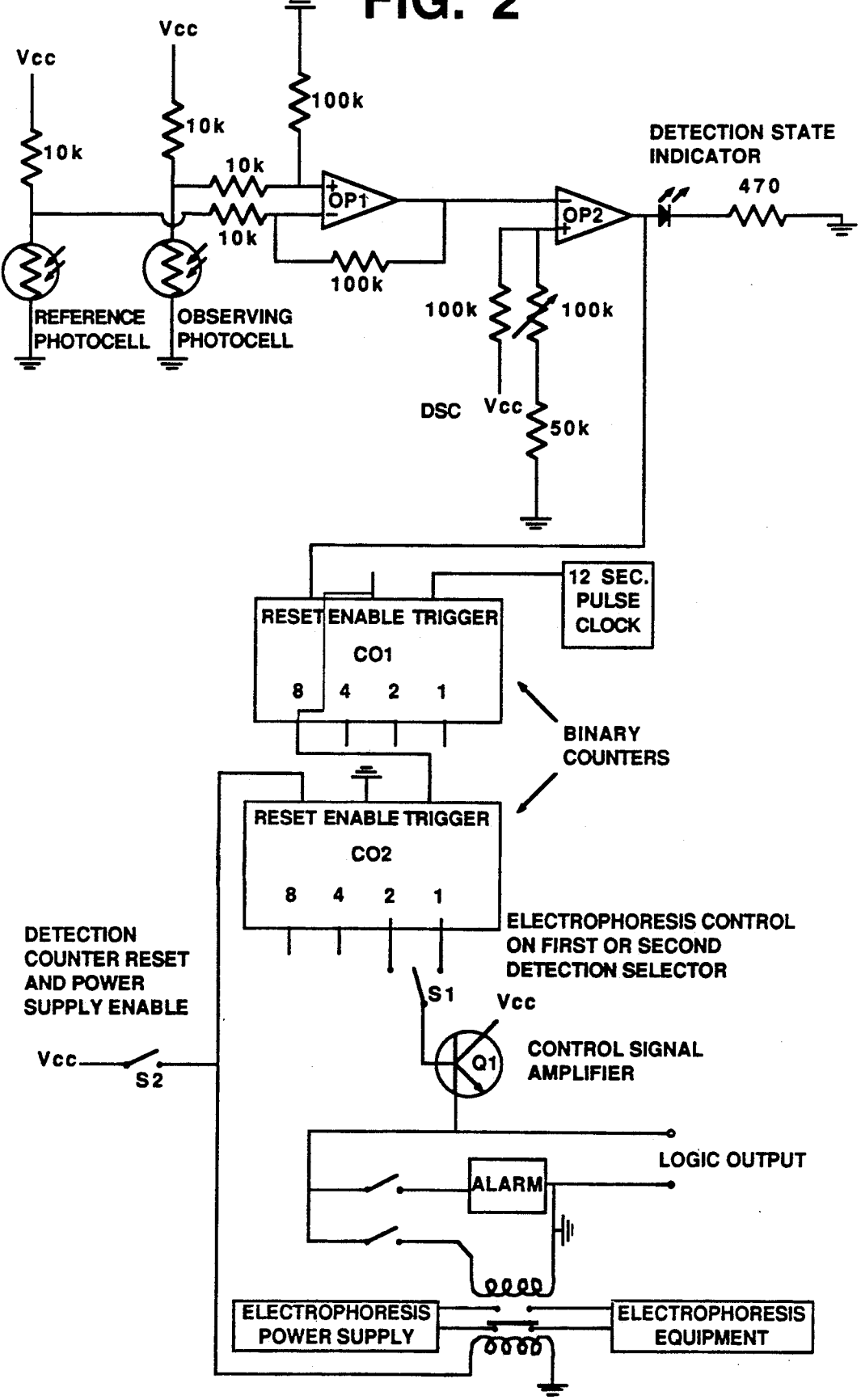
FIG. 2 is a circuit diagram which is an embodiment of the photoelectric electrophoresis controller shown in FIG. 1.

Referring now to FIG. 2 of the drawing, the amount of light falling on each of the two photocells generates a proportional voltage at the inputs of a differential operational amplifier OP1. A voltage proportional to the difference in the voltages obtained from the reference and observing photocells (Vref−Vobs) is applied to one input of a comparator amplifier OP2. The voltage provided by a Detection Sensitivity Control (DSC), for example a variable resistance voltage divider, is used to balance any intrinsic differences in the two photocell circuits or in the light falling on them during conditions of non-detection, such that the output of amplifier OP2 is kept "high" unless a transient difference in light between the photocells occurs (detection). The operator sets said control such that Detection State Indicator L1, a light-emitting diode, just remains lit during periods of non-detection.

While no detection is occurring, the "high" output of amplifier OP2 continuously resets a first counter CO1. However, should a state of detection keep the output of amplifier OP2 "low" for the duration, for example of eight pulses of a CLOCK, first the counter CO1 is frozen (disabled) for the remainder of that detection, and second the detection is counted by a second counter CO2. Spurious detections (those which are false, not genuine, or unqualified) are nullified if they last for less than eight pulses of the CLOCK. A switch S1 selects between the outputs of counter CO2, shown as pins 1 and 2, such that after the chsoen number of pulse detections (in this case, one or two), a transistor Q1 is driven to supply current foor electrophoresis control. Control options include termination of electrophoresis via disabling the supply of power to the apparatus, activating an alarm to notify a human operator, and providing a logic output that can trigger other devices such as automated sample processors, and automatic phone dialers and pages to notify operators at remote locations. Prior to operation, switch S2 is momentarily triggered to ensure that counter CO2 is set to zero and that the electrophoresis power supply is enabled.

Note that the 8-bit pin of counter CO1 is connected to both the trigger pin of counter CO2 and to its own enable pin. Accordingly, when the 8-bit pin of counter CO1 goes "high", counter CO2 counts a detection event, and counter CO1 is disabled during the remainder of that particular detection event, until counter CO1 is reset.

From the foregoing it will be understood that this photoelectric electrophoresis controller has features which enhance performance under certain conditions while limiting performance under others; however, the scope of this invention is not limited by said features. It is the located position of sample and/or marker molecules that is ensured.

The foregoing and various other objects and features of this invention will be apparent and fully understood from the detailed description of the typical preferred forms and application thereof, throughout which description reference is made to the accompanying drawings.

I claim:

1. A controller for an electrophoresis apparatus comprised of a gel matrix extending between electrodes of opposite polarity for the transport of molecules through said gel matrix, and including;
   a photodetector positioned at a gel matrix and comprised of at least one photocell to detect light from the electrophoresed molecules,
   a comparator amplifier in a circuit from the photocell and having a variable detection sensitivity control set for response to said light,
   and a detection state indicator in cirucit from the comparator amplifier for response to light detection set by said detection sensitivity control.

2. The electrophoresis controller as set forth in claim 1, wherein the photodetector is positioned to detect light through, light scattered from, and light emitted from the electrophoresed molecules.

3. The electrophoresis controller as set forth in claim 1, wherein the detection state indicator is an audible alarm.

4. The electrophoresis controller as set forth in claim 1, wherein the detection state indicator is a visible alarm.

5. The electrophoresis controller as set forth in claim 1, wherein the comparator amplifier has an output to a switch controlling a circuit through the electrodes.

6. The electrophoresis controller as set forth in claim 1, wherein the comparator amplifier has an output to a switch controlling a circuit through other equipment.

7. The electrophoresis controller as set forth in claim 1, wherein the comparator amplifier has an output circuit to a counter to quantify a number of detection events and trigger a control circuit after a preset number of detection events.

8. The electrophoresis controller as set forth in claim 7, wherein said counter is triggered by a clocked counter in circuit with the comparator amplifier for quantifying detection events for a preset time indicating a bona fide detection, whereby spurious detection is nullified.

9. A controller for determining position of molecules in an electrophoresis apparatus comprised of a gel matrix extending between electrodes of opposite polarity for the transport of molecules through said gel matrix, and including:
   a photodetector positioned at the gel matrix and comprised of a first observing photocell spaced from a second reference photocell and each to detect light from the electrophoresed molecules and the matrix,
   a differential amplifier in a circuit from each of said first and second photocells and a comparator amplifier in circuit from said differential amplifier and having a variable detection sensitivity control set for response,
   and a detection state indicator in circuit form the comparator amplifier for response to light differential detection set by said detection sensitivity control.

10. The electrophoresis controller as set forth in claim 9, wherein the photodetector is positioned to detect light through, light scattered from, and light emitted from the electrophoresed molecules.

11. The electrophoresed controller as set forth in claim 9, wherein the detection state indicator is an audible alarm.

12. The electrophoresis controller as set forth in claim 9, wherein the detection state indicator is a visible alarm.

13. The elecltrophoresis controller as set forth in claim 9, wherein the comparator amplifier has an output circuit to a counter to quantify a number of detection events and trigger a control circuit after a preset number of detection events.

14. The electrophoresis controller as set forth in claim 13 wherein said counter is triggered by a clocked counter in circuit with the comparator amplifier for quantifying detection events for a preset time indicating a bona fide detection, whereby spurious detection is nullified.

15. The electrophoresis controllers as set forth in claim 9, wherein the outputs of the first and second photocells are differentiated at the output of the differential amplifier as a differential voltage proportional to the difference in the photocell outputs, and wherein said differential voltage is compared to a threshold reference voltage applied to the comparator amplifier to produce distinct non detection-detection voltage at the output thereof.

16. The electrophoresis controller as set forth in claim 15, wherein the comparator amplifier has an output circuit to counter to quantify a number of detection events and trigger a control circuit after a preset number of detection events.

17. The electrophoresis controller as set forth in claim 16, wherein said counter is triggered by a clocked counter in circuit with the comparator amplifier for quantifying detection events for a preset time indicating a bone fide detection, whereby spurious detection is nullified.

18. The electrophoresis controller as set forth in claim 15, wherein said counter is triggered by a clocked counter in circuit with the comparator amplifier for quanifying detection events for a preset time indicating a bona fide detection, whereby spurious detection is nullified.

* * * * *